US00PP32122P2

(12) United States Plant Patent
Van Swieten

(10) Patent No.: US PP32,122 P2
(45) Date of Patent: Aug. 25, 2020

(54) ***PHALAENOPSIS* ORCHID PLANT NAMED 'PHALHOWLO'**

(50) Latin Name: ***Phalaenopsis* hybrid**
Varietal Denomination: PHALHOWLO

(71) Applicant: ANTHURA B.V., Bleiswijk (NL)

(72) Inventor: Martinus Nicolaas Gerardus Van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/602,201

(22) Filed: Aug. 27, 2019

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
CPC ... A01H 5/02; A01H 5/00; A01H 5/08; A01H 6/62
See application file for complete search history.

(56) References Cited

PUBLICATIONS

Upov Pluto Plant Variety Database 20200326, retrieved on Mar. 26, 2020, retrieved from the Internet at https://www.upov.int/pluto/en/index.jsp, one page. (Year: 2020).*

* cited by examiner

*Primary Examiner* — June Hwu
(74) *Attorney, Agent, or Firm* — Jondle & Associates, P.C.

(57) ABSTRACT

A new and distinct variety of *Phalaenopsis* plant named 'PHALHOWLO', particularly characterized by having white, shaded, flecked, and edged flowers with reddish-orange and very light purple lips, 1 to 2 peduncles that are long and sturdy, leaves that are oblong, and is propagated by meristem tissue culture, is disclosed.

3 Drawing Sheets

Genus and species: *Phalaenopsis* hybrid.
Variety denomination: 'PHALHOWLO'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHALHOWLO'.

The new *Phalaenopsis* plant is a product of a planned breeding program conducted by the inventor in Bleiswijk, the Netherlands. The objective of this breeding program was to create a new *Phalaenopsis* plant with numerous unique and attractive white, shaded, flecked, and edged flowers with reddish-orange and very light purple lips, suitable for potted plant production.

The new *Phalaenopsis* plant 'PHALHOWLO' is a result of cross-pollination made by the inventor in February 2011 in Bleiswijk, the Netherlands, of the proprietary female, or seed parent, *Phalaenopsis* hybrid '01-2112' (unpatented) with the proprietary male, or pollen parent, *Phalaenopsis* hybrid '21232-01' (unpatented).

The new *Phalaenopsis* was selected by the inventor as a single plant within the progeny of the stated cross-pollination in a controlled greenhouse in Bleiswijk, the Netherlands, in February 2014. Asexual reproduction of the new *Phalaenopsis* plant by meristem tissue culture since 2016 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Sep. 25, 2018, by Applicant who obtained the subject matter disclosed directly from the inventor. 'PHALHOWLO' has not been made publicly available or sold anywhere in the world prior to the effective filing date of this application with the exception of sales or disclosures made one year or less before the effective filing date of this claimed invention by Applicant who obtained 'PHALHOWLO' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHALHOWLO' as a new and distinct variety of *Phalaenopsis* plant:

1) White, shaded, flecked, and edged flowers with reddish-orange and very light purple lips;
2) 1 to 2 peduncles;
3) Peduncle is long and sturdy; and
4) Shape of the leaf is oblong.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in April 2019. Colors in the photographs may differ from the color values cited in the detailed botanical description, which accurately describe the actual colors of the new variety.

DESCRIPTION OF THE NEW VARIETY

Figure 1:
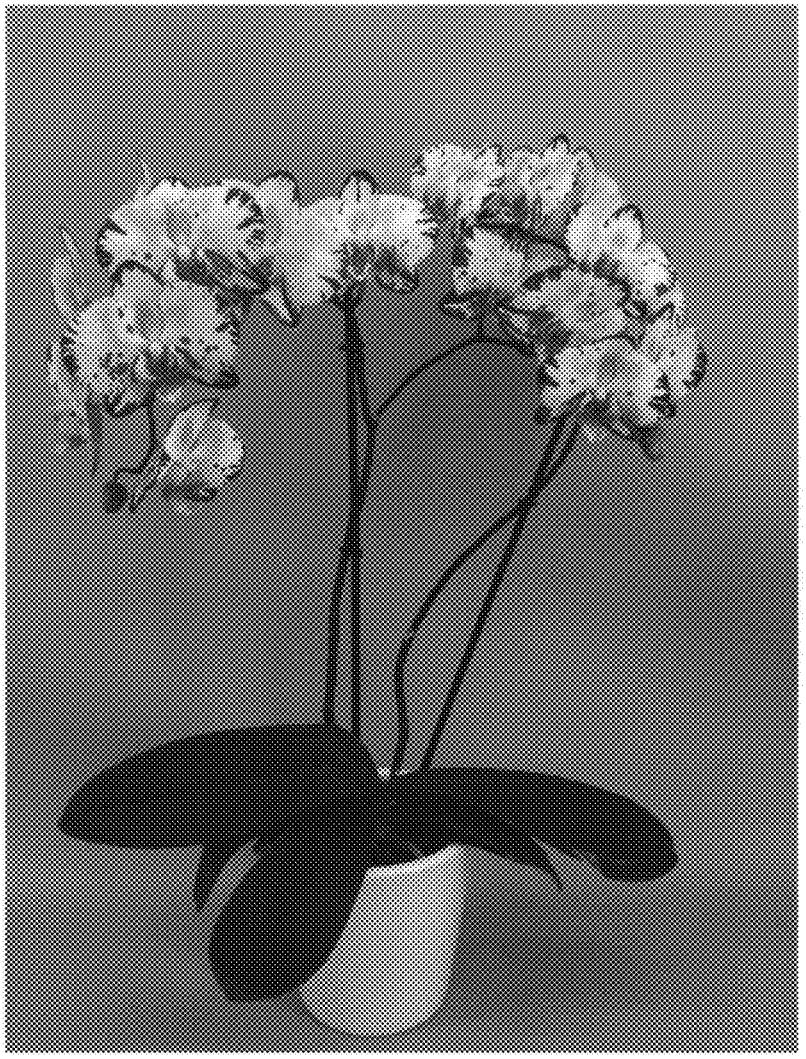
FIG. 1 shows the overall plant habit, including blooms, buds, and foliage of 'PHALHOWLO'.
Figure 2:
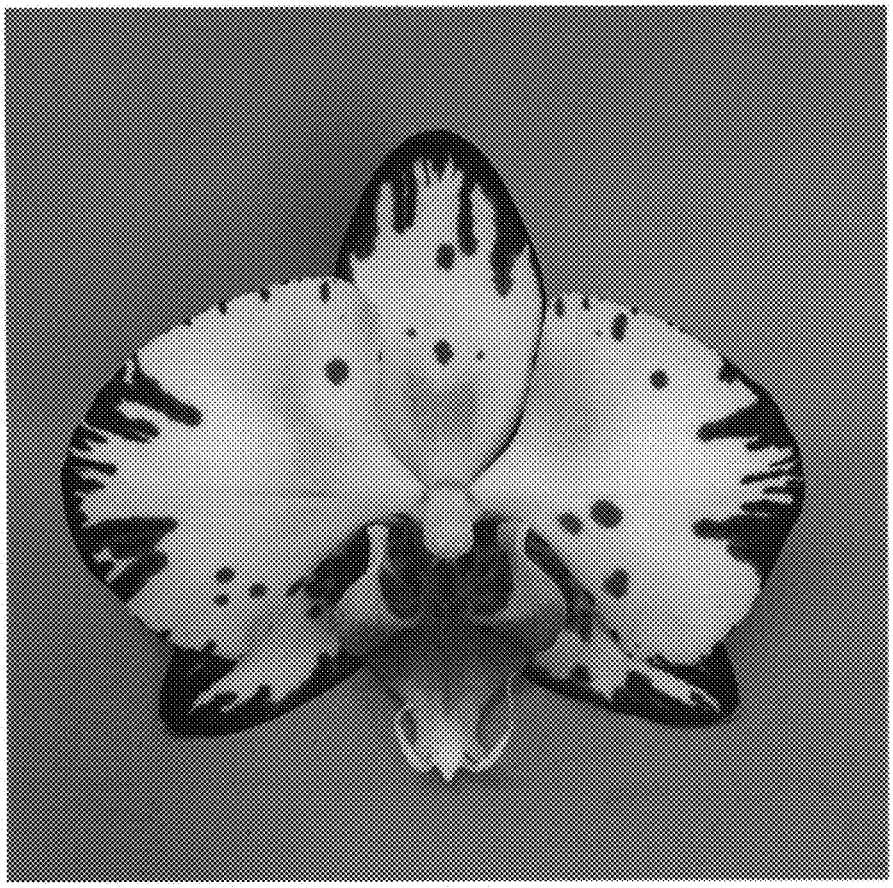
FIG. 2 shows a close-up of a flower of 'PHALHOWLO'.
Figure 3:
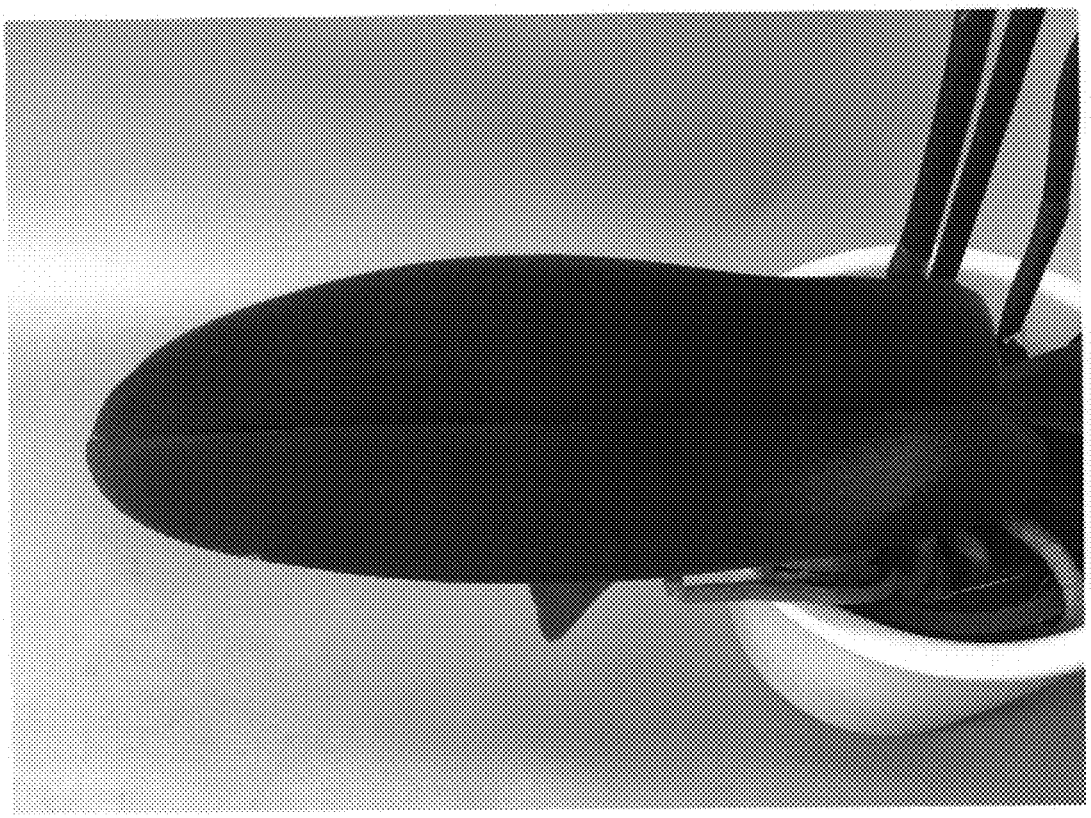
FIG. 3 shows an overhead view of the leaves of 'PHALHOWLO'.

The following detailed description sets forth the distinctive characteristics of 'PHALHOWLO'. Plants of the new *Phalaenopsis* have not been observed under all possible environmental conditions. The phenotype may vary somewhat with variations in environment such as temperature, light intensity and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in April 2019 on flowering plants which were planted in 12-centimeter (diameter) pots. After in-vitro propagation, the plants were grown in nursery trays for 20-24 weeks, followed by transplantation to 12-centimeter pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family.*—Orchidaceae.

*Botanical.*—*Phalaenopsis* hybrid.

*Common name.*—Moth orchid.

*Variety name.*—'PHALHOWLO'.

Parentage:

*Female parent.*—*Phalaenopsis* cultivar '01-2112' (unpatented).

*Male parent.*—*Phalaenopsis* cultivar '21232-01' (unpatented).

Propagation:

*Type.*—Meristem tissue culture.

Roots:

*Root description.*—Greyed-green (between RHS 190B and 190C) colored roots with branching lateral roots having yellow-green (RHS N144D) colored root tips with a touch of purplish-red (RHS N77B).

Plant:

*Commercial crop time to flowering.*—Following asexual propagation (in-vitro), the rooted cuttings grow for 20-24 weeks. After transplantation into 12-cm pots, the plants are finished after 48 to 50 weeks.

*Growth habit of peduncle.*—Upright to slightly pendant with raceme or panicle inflorescence.

*Height (from soil level to top of inflorescence).*—Approximately 55.0 cm to 60.0 cm.

*Width (measured from leaf tips).*—About 43.0 cm to 45.0 cm.

*Vigor.*—Sturdy.

Leaves:

*Mature leaves.*—Quantity per plant: 6 to 8 leaves are produced before flowering. Length (fully expanded): 21.0 cm to 24.0 cm. Width: 7.0 cm to 8.0 cm. Shape: Oblong. Base shape: Moderately elongated. Apex: Obtuse to rounded unequal. Leaf blade angle with the petiole (measured from the horizontal position): Between 5 degrees and 20 degrees. Leaf margin: Entire. Color: Upper surface: RHS 147A. Lower surface: RHS 147B. Spots (upper surface): Absent. Texture (both upper and lower surfaces): Rough. Thickness: 2.0 mm to 3.0 mm. Variegation: Absent. Venation: Pattern: Parallel. Color of the midvein: Upper surface: RHS 147A. Lower surface: RHS 146A.

Peduncle:

*Quantity per plant.*—1 to 2.

*Number of flowers per peduncle.*—8 to 16.

*Length.*—55.0 cm to 60.0 cm.

*Diameter.*—6.0 mm to 7.0 mm.

*Strength.*—Strong.

*Aspect.*—Upright to slightly pendant.

*Texture.*—Smooth.

*Color.*—Mix of brown (RHS N200A) and yellow-green (RHS 146C).

*Internode length.*—4.5 cm to 5.5 cm.

Inflorescence description:

*Appearance.*—Upright to slightly pendant, raceme or panicle inflorescence with bilaterally symmetrical flowers that open in succession beginning with the lowermost flower.

*Number of inflorescences.*—1 to 2.

*Inflorescence size.*—Height (from base to tip): 200.0 mm to 300.0 mm.

*Flowering time.*—First flowers can be expected 10 to 11 months after planting in a 12-cm pot.

*Flower.*—Height: 74.0 mm to 79.0 mm. Diameter: 93.0 mm to 98.0 mm. Depth of lip: 27.0 mm to 29.0 mm.

*Flower longevity.*—On the plant: 11 to 16 weeks.

*Fragrance.*—Absent.

*Flower bud.*—Average size: Large. Length: 20.0 mm to 22.0 mm. Width: 16.0 mm to 18.0 mm. Shape: Egg shaped. Color: Purplish-red (RHS 183D) at the base and light yellow-green (between RHS 145B and 145C) toward the tip.

*Petals.*—Arrangement: Open/free. Curvature at longitudinal axis: Recurving. Shape: Semi-circular. Shape in cross section: Convex. Presence of any twisting: Absent. Apex: Rounded asymmetric. Margin: Slightly undulated. Intensity of undulation of the margin: Moderate. Length (from base to tip): 43.0 mm to 45.0 mm. Width: 52.0 mm to 54.0 mm. Position of the broadest part of the petal: Toward the base. Color (when fully opened): Upper surface: Basic color: White (RHS NN155C). Over color: Light purple (RHS 76A) at the base; flecked (RHS N79C) with dark purplish-red stripes (between RHS N79B and N79C) at the edge. Number of dots and stripes: Few dots and few stripes. Size of dots and stripes: Small to medium dots and medium stripes. Lower surface: Basic color: White (RHS NN155C). Over color: Light reddish-purple (RHS N78D) at the base and diluting stripes (between RHS N79C and N79D) at the edge.

*Dorsal sepal.*—Curvature at longitudinal axis: Incurving. Shape: Elliptic. Shape in cross section: Concave. Presence of any twisting: Absent. Apex: Obtuse symmetric. Margin: Entire. Intensity of undulation of the margin: Absent. Length (from base to tip): 45.0 mm to 47.0 mm. Width: 28.0 mm to 30.0 mm. Color (when fully opened): Upper surface: Basic color: White (RHS NN155C). Over color: Purplish-pink (RHS N78C) at the base and dark purplish-red flecks and stripes (between RHS N79B and N79C) at the edge. Number of dots and stripes: Few dots and few stripes. Size of dots and stripes: Small to medium dots and medium stripes. Lower surface: Basic color: White (RHS NN155C). Over color: Slightly light yellow-green (RHS 145C) at the base and light reddish-purple (RHS N78D) in the middle; diluting reddish-purple (RHS N79D) at the edge.

*Lateral sepals.*—Shape: Ovate. Apex: Obtuse asymmetric. Margin: Entire. Length (from base to tip): 46.0 mm to 48.0 mm. Width: 25.0 mm to 27.0 mm. Color (when fully opened): Upper surface: Basic color: White (RHS NN155C). Over color: Slightly light yellow-green (RHS 145C), light reddish-purple (RHS N78A), and dotted (RHS 183C) at the base; dark purplish-red midvein and stripes (between RHS N79B and N79C) toward edge. Number of dots and stripes: Medium dots and few stripes. Size of dots and stripes: Small to medium dots and medium stripes. Lower surface: Basic color: White (RHS NN155C). Over color: Slightly light yellow-green (RHS 145D) and purplish-red (RHS N77B) at the base; diluting dark purplish-red stripes (between RHS N79C and N79D) toward edge.

*Labellum* (*lip*).—Whiskers: Present. Length of whiskers: 13.0 mm to 15.0 mm. Color of whiskers: Very light purple (RHS 76B) with few pink dots (RHS 182C) and light yellow tips (RHS 10B). Pubescence on the lip: Absent.

*Lateral lobe.*—Shape: Type V (as described in the International Union for the Protection of New Varieties of Plants (UPOV) Test Guidelines for *Phalaenopsis*); spatulate. Curvature: Weak. Margin: Undulated. Length: 19.0 mm to 21.0 mm. Width: 15.0 mm to 17.0 mm. Color: Yellow (RHS 12B) with dark reddish-orange stripes (RHS 175B to 175C) at the base; dark reddish-orange (RHS 175C) and yellow (RHS 12B) on one side; white (RHS NN155C) toward other side. Number of stripes and netting: Few stripes. Fusion of the lateral lobes to the apical lobe: None.

*Apical lobe.*—Shape: Triangular. Margin: Entire. Length: 20.0 mm to 22.0 mm. Width: 19.0 mm to 21.0 mm. Color: Slightly yellow (RHS 12B) and dark reddish-orange (RHS 175B) at the base; very light purple (RHS 76C); dotted (RHS 182C). Number of stripes and netting: None.

*Callus.*—Average size: Medium. Height: 6.0 mm to 7.0 mm. Length: 5.0 mm to 6.0 mm. Width: 4.0 mm to 5.0 mm. Color: Yellow (RHS 17B); striped and dotted (RHS 175B to 175C).

Reproductive organs:

*Column.*—Length: 8.0 mm to 10.0 mm. Diameter: 4.9 mm to 5.4 mm. Color: White (RHS NN155C) with very light purple shade (RHS 76C).

*Pollinia.*—Quantity: 2. Diameter: 0.9 mm to 1.2 mm. Color: Orange (RHS 24A).

*Ovary.*—Length: 9.0 mm to 11.0 mm. Diameter: 2.4 mm to 2.7 mm. Color: Light yellow-green (RHS 145D) and light reddish-purple (RHS N78D) toward the flower.

*Pedicel.*—Length: 41.0 mm to 43.0 mm. Diameter: 2.9 mm to 3.3 mm. Color: Purple (RHS N77A) at the base; purplish-red (RHS N77B) and light yellow-green (RHS 145D) toward the flower.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHALHOWLO' differs from female parent plant '01-2112' (unpatented) in that 'PHALHOWLO' has rounded petal apexes and flowers with a shaded, flecked, and edged pattern, whereas '01-2112' has obtuse to rounded petal apexes and flowers with a centered pattern. Additionally, 'PHALHOWLO' has larger flowers than '01-2112'.

'PHALHOWLO' differs from male parent plant '21232-01' (unpatented) in that 'PHALHOWLO' has rounded petal apexes and flowers with a shaded, flecked, and edged pattern, whereas '21232-01' has emarginated petal apexes and flowers with an even pattern. Additionally, 'PHALHOWLO' has larger flowers than '21232-01'.

'PHALHOWLO' is most similar to the commercial *Phalaenopsis* plants named 'PHALDOPFO' (U.S. Plant Pat. No. 29,452) and 'PHALGULFQ' (U.S. Plant Pat. No. 29,975). 'PHALHOWLO' differs from the commercial variety 'PHALDOPFO' in that 'PHALHOWLO' has obtuse dorsal sepal apexes and whiskers that are very light purple with pink dots and light yellow tips, whereas 'PHALDOPFO' has rounded to slightly emarginated dorsal sepal apexes and whiskers that are white with a purple stripe in the middle. Additionally, 'PHALHOWLO' has smaller flowers, shorter whiskers, and longer leaves than 'PHALDOPFO'.

'PHALHOWLO' differs from the commercial variety 'PHALGULFQ' in that 'PHALHOWLO' has rounded petal apexes and whiskers that are very light purple (RHS 76B) with pink dots and light yellow tips, whereas 'PHALGULFQ' has obtuse petal apexes and whiskers that are light purple (RHS 76D).

I claim:

1. A new and distinct variety of *Phalaenopsis* plant named 'PHALHOWLO', substantially as described and illustrated herein.

* * * * *